(12) United States Patent
Benyacoub et al.

(10) Patent No.: US 9,226,521 B2
(45) Date of Patent: *Jan. 5, 2016

(54) INFANT FORMULA WITH PROBIOTICS AND MILK FAT GLOBULE MEMBRANE COMPONENTS

(75) Inventors: Jalil Benyacoub, Lausanne (CH); Stephanie Blum-Sperisen, Pully (CH); Mohamed Nabil Bosco, Epalinges (CH); Lionel Jean Rene Bovetto, Larringes (FR); Isabelle Bureau-Franz, Paris (FR); Anne Donnet-Hughes, Saint-legier (CH); Eduardo Schiffrin, Crissier (CH); Laurent Favre, Servion (CH)

(73) Assignee: Nestec S.A., Vevey (CH)

( * ) Notice: Subject to any disclaimer, the term of this patent is extended or adjusted under 35 U.S.C. 154(b) by 190 days.

This patent is subject to a terminal disclaimer.

(21) Appl. No.: 13/514,513

(22) PCT Filed: Dec. 7, 2010

(86) PCT No.: PCT/EP2010/069016
§ 371 (c)(1),
(2), (4) Date: Jun. 7, 2012

(87) PCT Pub. No.: WO2011/069987
PCT Pub. Date: Jun. 16, 2011

(65) Prior Publication Data
US 2012/0321600 A1    Dec. 20, 2012

(30) Foreign Application Priority Data
Dec. 8, 2009  (EP) .................... 09178339

(51) Int. Cl.
| | | |
|---|---|---|
| *A61K 35/74* | (2015.01) | |
| *A23L 1/29* | (2006.01) | |
| *A23L 1/30* | (2006.01) | |
| *A23L 1/305* | (2006.01) | |
| *A61K 35/20* | (2006.01) | |

(52) U.S. Cl.
CPC ............... *A23L 1/296* (2013.01); *A23L 1/3006* (2013.01); *A23L 1/3014* (2013.01); *A23L 1/3056* (2013.01); *A61K 35/20* (2013.01); *A61K 35/74* (2013.01); *A23C 2240/05* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 5,635,401 A | * | 6/1997 | Spitsberg et al. | ................ 436/23 |
| 7,651,680 B2 | * | 1/2010 | Breton et al. | .............. 424/78.02 |
| 2008/0003330 A1 | | 1/2008 | Rueda et al. | |

FOREIGN PATENT DOCUMENTS

| | | |
|---|---|---|
| FR | 2908605 A1 | 5/2008 |
| UA | 30063 | 2/2008 |
| WO | 2004/112509 A2 | 12/2004 |
| WO | 2006/041316 A1 | 4/2006 |
| WO | 2007/009187 A1 | 1/2007 |

OTHER PUBLICATIONS

Moe et al. (http://www.chese2008.ch/download.php?filename=moe_1.pdf)., 2008.*
Fox et al., Australian Journal of Dairy Technology 1998, 53(2), 83-89.*
Nighswonger et al. , http://www.ansi.okstate.edu/research/research-reports-1/1995/1995-1%20Nighswonger.pdf, (accessed Nov. 15, 2013).*
Astaire et al. J. Dairy Sci. vol. 86, pp. 2297-2307, 2003.*
Martin et al., J Pediatr. 2003;143:754-8.*
Cavaletto et al.. Clinica Chimica Acta 347 (2004) 41-48.*
Burns et al., International Journal of Dairy Technology, vol. 61, No. 2 May 2008, pp. 156-164.*
Petschow et al., J Clin Gastroenterol. Oct. 2005;39(9):786-90.*
Written Opinion and International Search Report issued May 27, 2011 for corresponding Intl. Appln. No. PCT/EP2010/069016.
Rodas et al. "Preparation of probiotic buttermilk with Lactobacillus reuteri" Milchwissenschaft, 2002, vol. 57, pp. 26-28.
Domellof et al. "Processed Infant Cereals as Vehicles of Functional Components" Nestle Nutr. Workshop Ser. Pediatr. Program, 2007, vol. 60, pp. 107-121.

* cited by examiner

*Primary Examiner* — Irene Marx
(74) *Attorney, Agent, or Firm* — K&L Gates LLP

(57) ABSTRACT

A nutritional composition is proposed comprising a probiotic and milk fat globule membrane (MFGM) wherein the MFGM and the probiotics mutually potentiate their respective effects and promote complementary beneficial protective mechanisms that reflect physiological synergy. The nutritional composition can be an infant formula, infant cereals, baby food or health care nutritional product. The synergistic effect can include promoting immune maturation and/or immune education and/or reducing inflammation and/or treating or preventing disease or infections.

12 Claims, 6 Drawing Sheets

Figure 1:
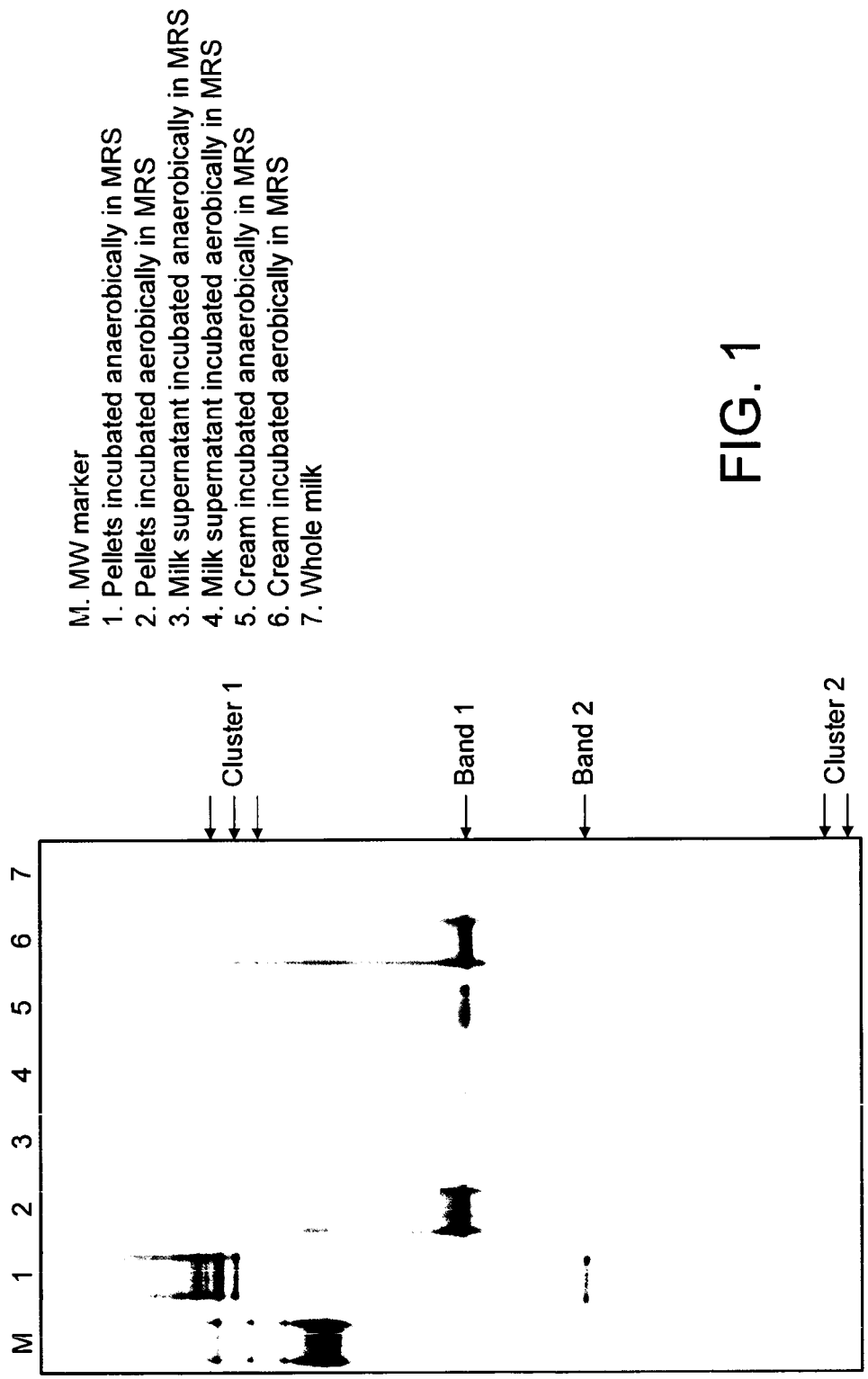

M. MW marker
1. Mother#1, supernatant (nested PCR)
2. Mother#1, pellet (direct PCR)
   Cream Mother#1 is identical to the pellet
3. Mother#2, cream (nested PCR)
4. Mother#2, supernatant (nested PCR)
5. Mother#2, pellet (direct PCR)
6. Mother#2, aerobically incubated total milk (nested PCR)
7. Mother#2, anaerobically incubated total milk (direct PCR)

INFANT FORMULA WITH PROBIOTICS AND MILK FAT GLOBULE MEMBRANE COMPONENTS

CROSS REFERENCE TO RELATED APPLICATIONS

The present application is a National Stage of International Application No. PCT/EP2010/069016, filed on Dec. 7, 2010, which claims priority to European Patent Application No. 09178339.9, filed on Dec. 8, 2009, the entire contents of which are being incorporated herein by reference.

This invention relates to an infant formula with probiotics and Milk Fat Globule Membranes components (MFGM) and/or bioactive proteins.

Mother's milk is recommended for all infants. However, in some cases breast feeding is inadequate or unsuccessful for medical reasons or the mother chooses not to breast feed. Infant formulas have been developed for these situations.

In the recent past, certain strains of bacteria have attracted considerable attention because they have been found to exhibit valuable properties for man if ingested. In particular, specific strains of the genera Lactobacilli and Bifidobacteria have been found to be able to colonize the intestinal mucosa, to reduce the capability of pathogenic bacteria to adhere to the intestinal epithelium, to have immunomodulatory effects and to assist in the maintenance of well-being. Such bacteria are called probiotics.

Extensive studies have been carried out to identify new probiotic strains. For example, EP 0 199 535, EP 0 768 375, WO 97/00078, EP 0 577 903 and WO 00/53200 disclose specific strains of Lactobacilli and Bifidobacteria and their beneficial effects.

Immediately before birth, the gastro-intestinal tract of a baby is thought to be sterile. During the process of birth, it encounters bacteria from the digestive and genital tracts and skin of the mother and starts to become colonized. Post-natal colonization of the gastro-intestinal tract with commensal bacteria provides bacterial stimuli that are crucial for the functional development of the major compartments of the gut associated lymphoid tissue (GALT) comprising Peyer's patches (T and B cells, macrophages, dendritic cells), lamina propria (T cells, IgA plasma B cells, dendritic cells, mast cells) and intraepithelial lymphocytes (natural killer cells, T cells). This process is in large part responsible for the sentinel capacity of gut immune cells to distinguish harmless and danger signals and as a consequence establish tolerance or immunity.

Large differences exist with respect to the composition of the gut microbiota in response to the infant's feeding. The fecal flora of breast-fed infants includes appreciable populations of Bifidobacteria with some *Lactobacillus* species, whereas formula-fed infants have more complex microbiota, with Bifidobacteria, Bacteroides, Clostridia and Streptococci all usually present.

For this and other reasons, it has been proposed to add probiotics to infant formulas. Specific probiotic strains have been shown to stimulate immune defense mechanisms, antagonize pathogenic bacteria, promote a healthy microbiota, and down-regulate immune-related disorders such as allergies or inflammation in animals and humans. The ability of specific probiotic bacterial strains to modulate the components of the intestinal microbiota of the host is one mechanism by which they affect the immune system. In addition, a direct interaction with the mucosal immune system to stimulate the generation of immune-regulating cytokines has also been postulated and is further supported by recent findings of possible direct sampling of luminal bacteria by dendritic cells that extend dendrites across the intestinal epithelium.

More recently, Benyacoub et al. have demonstrated that early life supplementation with *Lactobacillus rhamnosus* CGMCC 1.3724 is able to promote mucosal immune defenses and increase response to systemic vaccine in a neonatal mouse model (J Benyacoub, A Zuercher, R Bibiloni, K-Y Saudan, P Serrant, G Reuteler, I Rochat, I Segura-Roggero, F Foata, K Deiser, K Vidal, F Rochat, S Blum. Early life feeding with low dose *Lactobacillus rhamnosus* CGMCC 1.3724 promotes immune development in gnotobiotic mice. Acta Pædiatrica 2007, 96 (Suppl. 456), pp. 12). Other recent advances in research suggest that human breast milk contains a low dose of bacteria and/or bacterial fractions, naturally originating from the mother's gut, that seem to be transmitted to the infant (Pablo F. Perez, Joël Doré, Marion Leclerc, Florence Levenez, Jalil Benyacoub, Patrick Serrant, Iris Segura-Roggero, Eduardo J. Schiffrin, and Anne Donnet-Hughes. Bacterial Imprinting of the Neonatal Immune System: Lessons From Maternal Cells? PEDIATRICS Volume 119 (3), March *Pediatrics* 2007: 119; 724-732.) It is hypothesized that this inoculum after birth contributes to the early education of the infant's immune system.

WO 2007/009187 A1 discloses the use of sour cream or buttermilk with probiotics. Burn et al (P. Burns, G Vinderola, F Molinari, J. Reinhemer. (2008) Suitability of whey and buttermilk for the growth and frozen storage of probiotic lactobacilli, International Journal of Dairy Technology 61, Issue 2, 156-164) discloses in the abstract the use of whey or buttermilk as culture media for the growth and storage of probiotic lactobacilli.

Rodas et al (B. A. Rodas, J. O. Angulo, J. Cruz, H. S. Garcia (2002). Preparation of probiotic buttermilk with *Lactobacillus reuteri*. Milchwissenschaft, 57(1), 26-28) discloses the use of *Lactobacillus reuteri* to prepare a probiotic buttermilk.

UA 30 063 discloses a drink comprising buttermilk, or a mix of buttermilk with cheese whey, or a mix of buttermilk with nonfat milk and cheese whey as the milk vehicle together with a symbiotic probiotic starter culture of specific bifidobacteria and lactobacilli.

The above disclosures discuss the chemical & physical (solubility, viscosity, emulsifying and foaming) properties of different sources of buttermilk or discuss the use of cream or buttermilk as carriers or as storage or growth media for probiotics; or to provide fermented products with improved technological or organoleptic properties.

WO 2004/112509, provides an infant formula preparation containing MFGM and at least one microorganism for inducing a maturation of the physical barrier provided by the intestine in manner that is similar to that obtained with breast-feeding.

US 2008/0003330 A1 describes the use of an enriched whey protein concentrate containing MFGM, to provide bioactive lipids for brain and cognitive development and function in the infant.

FR 2908605 A1 discloses a nutritional product containing MFGM as a source of lipids for application in the gastrointestinal tract. It also discloses the use of specific strains of lactic acid bacteria. However, these bacteria are considered for their technological properties and not as probiotics. The present invention extends the use of MFGM to its use with probiotics with specific health benefits.

For the benefit of infants that will not be completely breast fed, there is a continuing need to develop infant formulas which will replicate human milk as close as possible, both in terms of its nutritional and its bioactive properties.

SUMMARY OF THE INVENTION

The invention relates to a composition, preferably an infant formula, comprising probiotics and MFGM. The invention also relates to a composition for educating the immune system, promoting immune maturation, promoting immune maturation, and for treating or preventing a range of physio-pathological conditions such as treating or preventing inflammation, treating or preventing infections, treating or preventing dysregulated gut barrier function, improving gut comfort or combination thereof. The invention is more particularly suitable for use in infants, pre-term infants, babies or individuals in needs.

SHORT DESCRIPTION OF THE DRAWING

FIG. 1: Human Milk from 1 mother, 7 days postpartum. Bacterial DNA (Bands 1 and 2) appearing in particular in samples 5 and 6, i.e. in the cream fractions containing MFGM).

Figure 2:
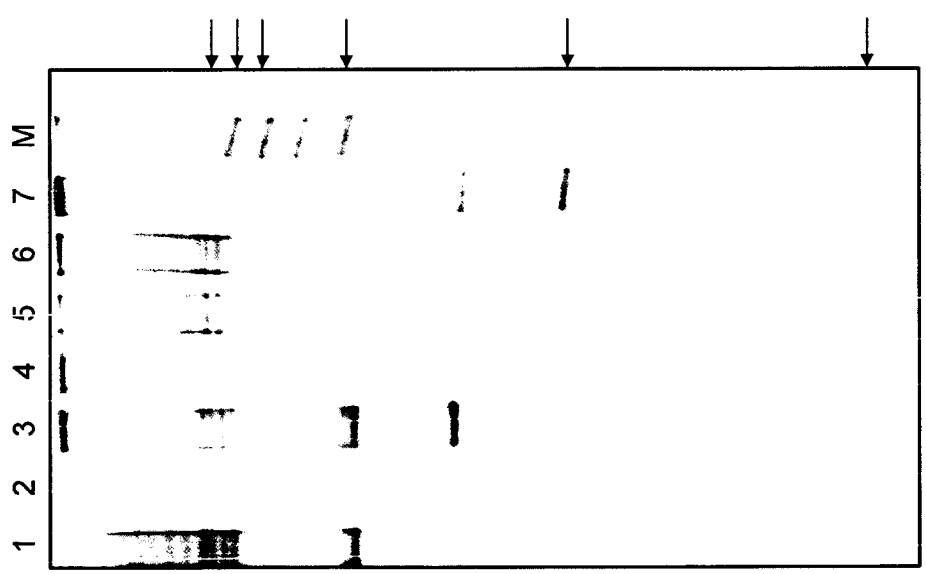

FIG. 2: Human Milk from 2 mothers, Bacterial DNA (Bands indicated by the middle 2 arrows) appearing in particular in samples 2 and 3, i.e in the cream fractions containing MFGM).

Figure 3:
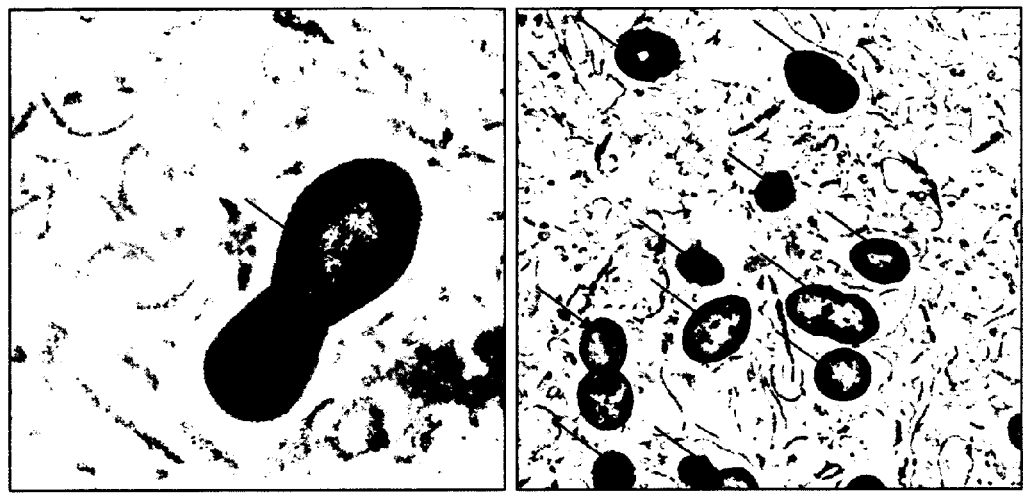

FIG. 3: Electron micrographs of MFGM (NRC, F. Morgan) showing bacterial structures alone or in chains (marked with arrows), associated with the MFGM.

Figure 4:
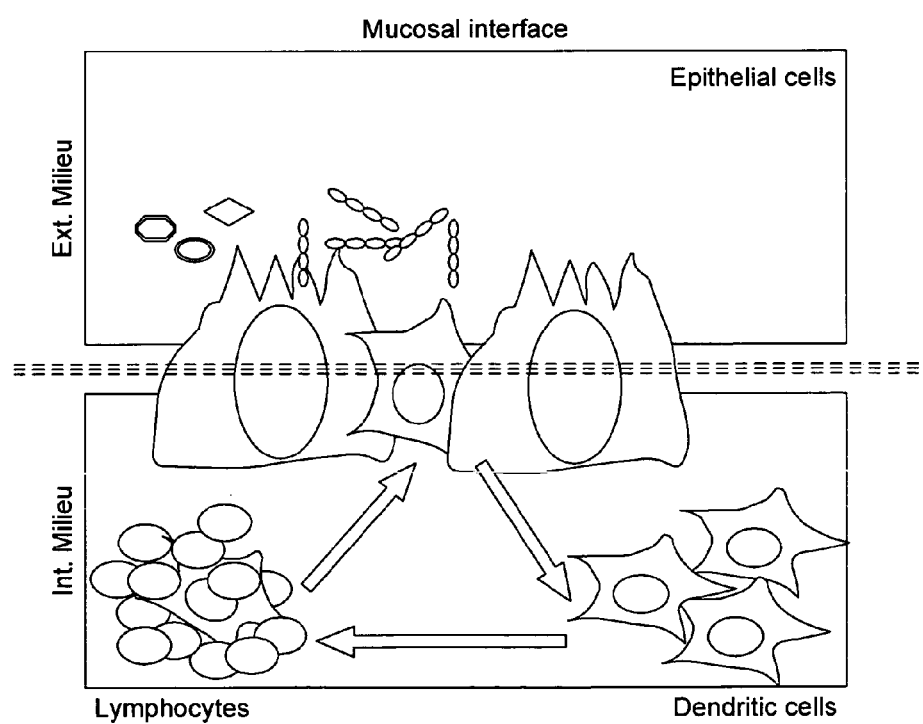

FIG. 4: Model of mucosal cell interactions

Figure 5:
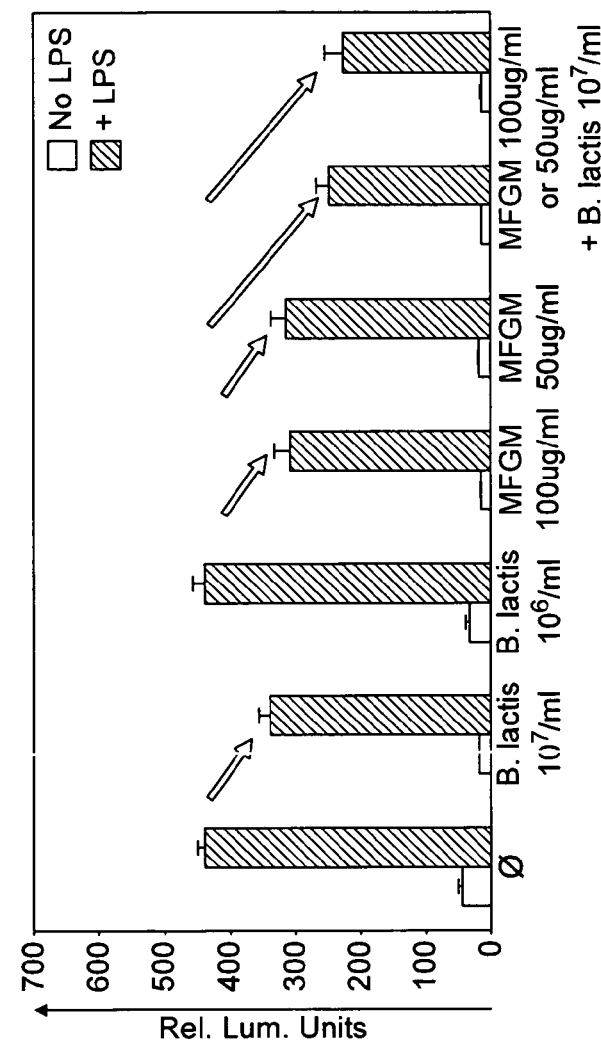
Figure 5:
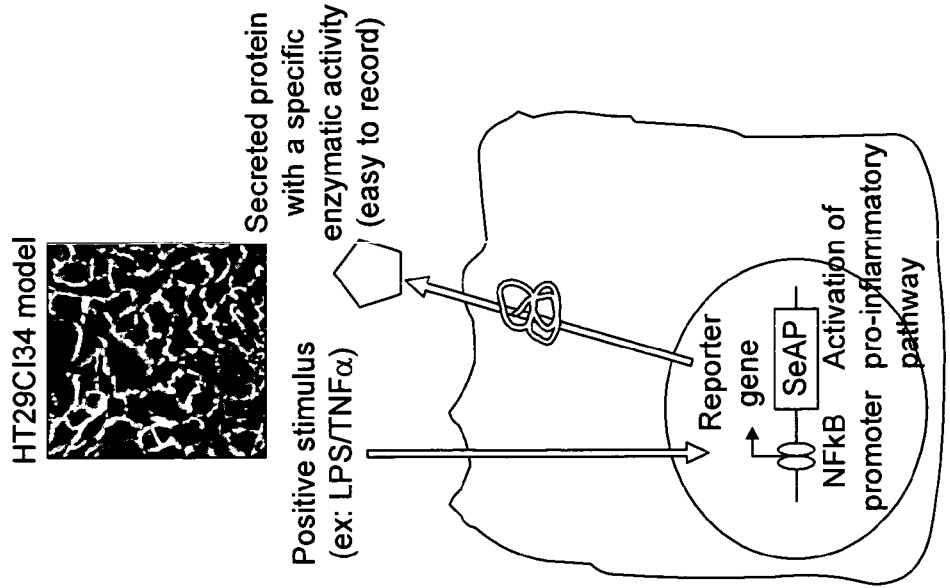

FIG. 5: Epithelial cell response to LPS. Probiotics and MFGM lower epithelial cells responsiveness to endotoxin challenge (LPS) and related inflammatory reaction. A cumulative effect could be observed with the combination of probiotics and MFGM, suggesting a synergy between the two ingredients.

Figure 6:
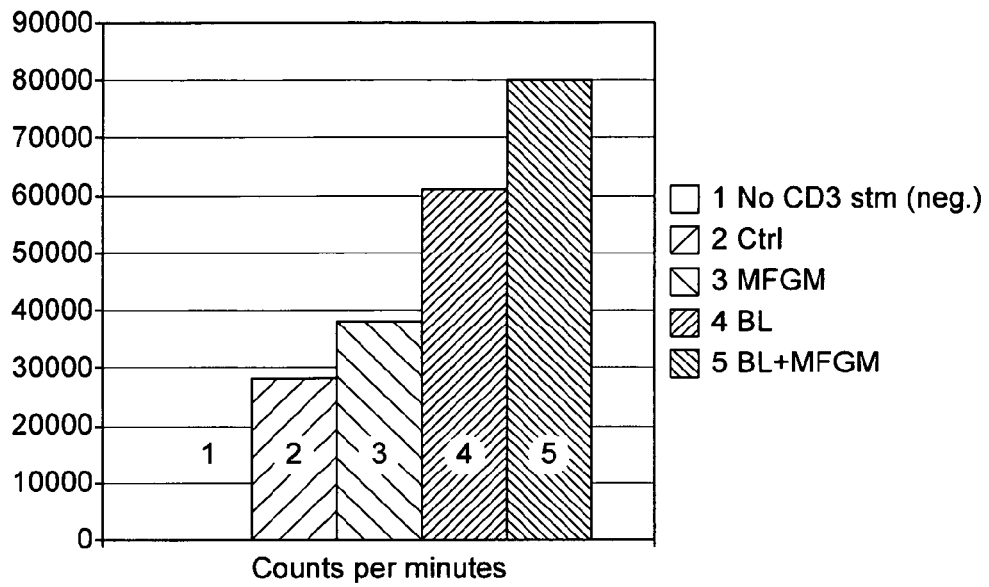

FIG. 6: T cell activation. MFGM and probiotics promote T lymphocyte activation. A synergy could be observed between MFGM and *B. lactis*.

Figure 7:
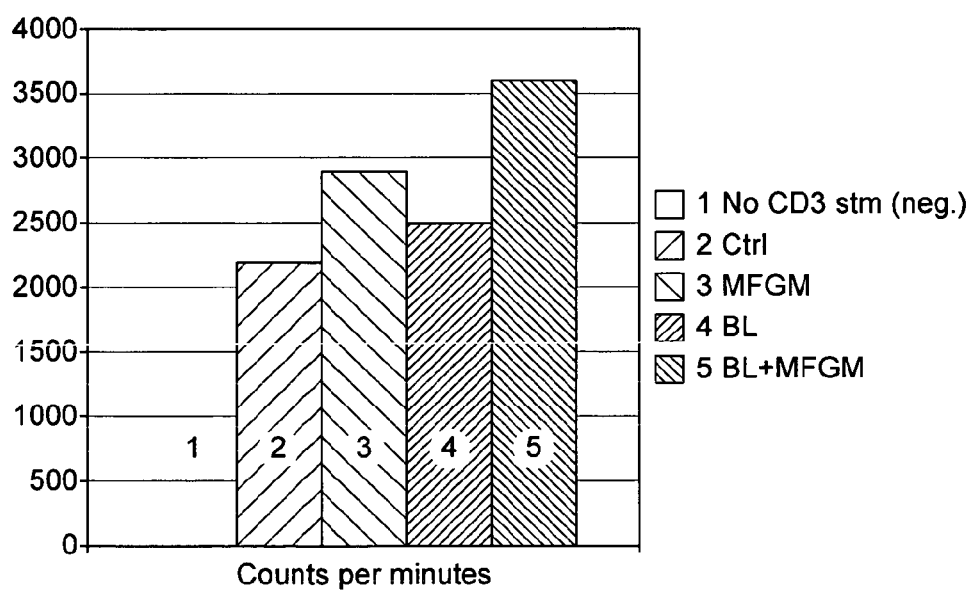

FIG. 7: B cell activation. MFGM promotes B lymphocyte activation. Probiotics alone are less effective. A synergy could be observed between MFGM and probiotics.

Figure 8:
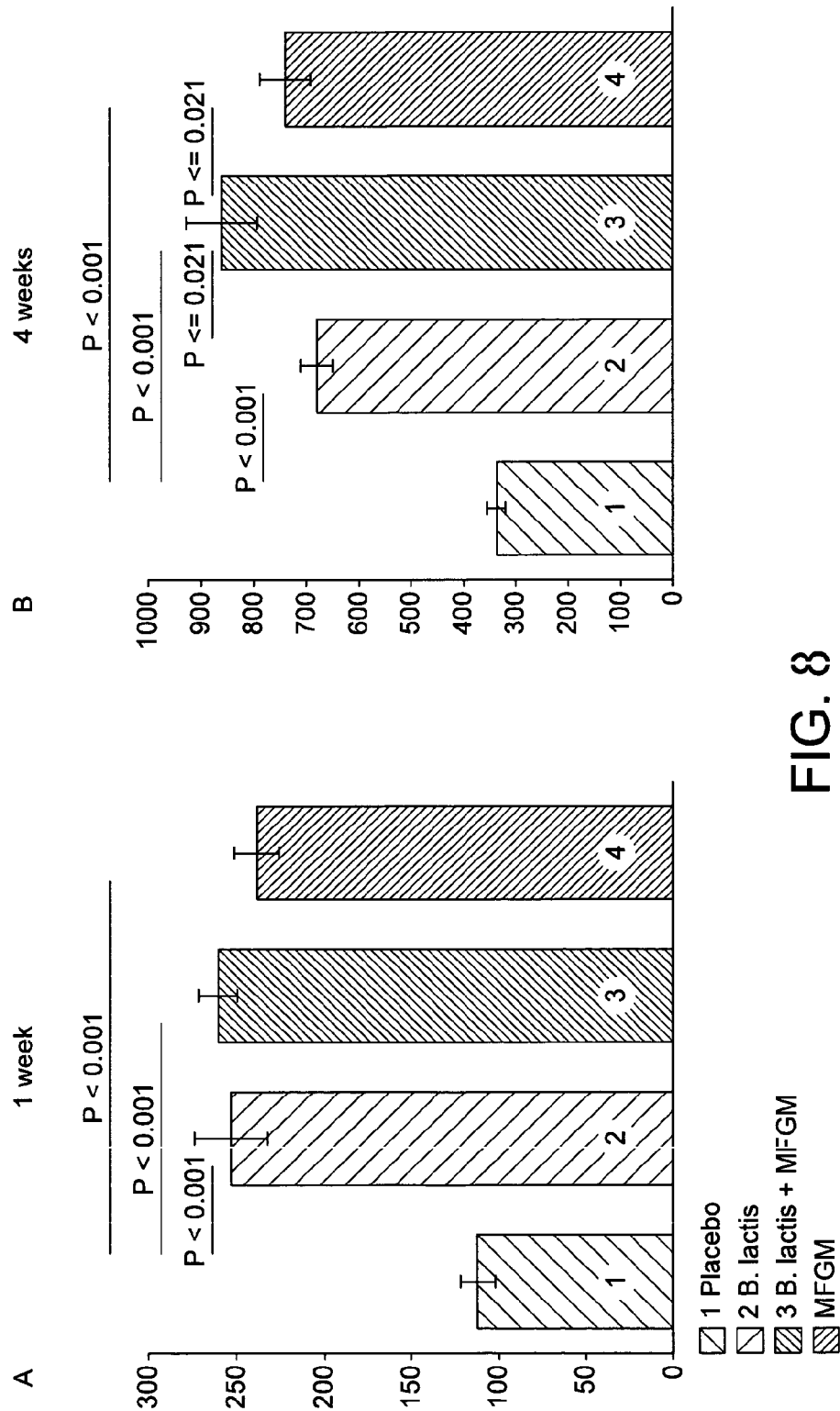

FIG. 8: Non-specific intestinal IgA production. IgA-secreting cells levels isolated from Peyer's patches of mice fed MFGM for 1 week (A) and 4 weeks (B).

DETAILED DESCRIPTION OF THE INVENTION

Definition

In this specification, the following terms have the meaning assigned to them below: "infant" means a child under the age of 36 months;

"infant formula" means a foodstuff intended for the complete nutrition of infants during the first 12 months of life; In the context of the invention this applies more particularly to infants up to the age of 6 months.

"individual in need" means any infant, baby, child, adolescent or adult having particular physiological needs in regard to the physio-pathological conditions considered and for which the proposed invention offers an improved or alternative solution. This includes patients of all ages suffering from such physio-pathological conditions.

"prebiotic" means a non-digestible food ingredient that beneficially affects the host by selectively stimulating the growth and/or activity of one or a limited number of bacteria in the colon and thus improves host health (Gibson and Roberfroid "Dietary Modulation of the Human Colonic Microbiota: Introducing the Concept of Prebiotics" J. Nutr 125: 1401-1412).

"probiotic" means, in the context of bacterial strains, microbial cell preparations or components of microbial cells with a beneficial effect on the health or well-being of the host. (Salminen S, Ouwehand A. Benno Y. et al "Probiotics: how should they be defined" Trend Food Sci. Technol. 1999:10 107-10);

"the first few weeks of the life of an infant" means the period up to the end of the second month of life of the infant.

"Milk Fat Globule Membrane (MFGM)" are fatty fractions of milk (in particular cow milk or human milk) as described and defined in *Nutritional and technological aspects of milk fat globule membrane material*, International Dairy Journal 18 (2008) 436-457, K. Dewettinck et al. In short, the term encompasses the membrane and membrane-associated materials that surround fat globules in mammalian milk, together with the other components of MFGM, referred to as "MFGM components". For ease of language in the present document, the terms "MFGM" and "MFGM components" are used interchangeably.

The present inventors recently observed that bacteria in human milk are associated inter alia with the cream fraction of the milk. This discovery prompted further investigations into the association of bacteria and lipid as well as protein components in human milk and the effects of this association leading to the present invention.

In one embodiment the present invention provides a nutritional composition comprising a probiotic bacterial strain in an amount equivalent to from $10^3$ to $10^{12}$ cfu/g of dry formula and milk fat globule membrane (MFGM) in an amount of from 0.01 g to 0.1 g for 100 g of liquid composition or formula, preferably from 0.03 to 0.1 g for 100 g of liquid composition or formula, and/or from 0.01 g to 0.8 g for 100 g of dry composition or formula, preferably from 0.1 to 0.5 g for 100 g of dry composition or formula. In one embodiment the composition comprises MFGM in an amount of between 0.1% and 10% w/w of total proteins, preferably between 0.5% and 5%. In one embodiment the nutritional composition comprises MFGM in an amount between 0.01 g and 7 g of MFGM per 100 g of composition (w/w).

In one embodiment the invention MFGM originates from bovine, buffalo, horse, goat and/or human milk.

The Human milk fat globule membrane protein composition is still largely unknown, although it counts for 2-4% of the total milk protein content (Stephania Quaranta et al. Human proteome enhancement: High-recovery method and improved two dimensional map of colostral fat globule membrane proteins. Electrophoresis 2001, 22, 1810-1818). The invention encompasses an amount of Human milk fat globule membrane ranging from 0.1% to 10% of the total protein of the composition or formula, preferably from 0.5% to 2% of the total protein of the composition or formula The invention also extends to the use of a probiotic bacterial strain and milk fat globule membrane in the manufacture of a nutritional composition for promoting the maturation of the immune system of a neonatal infant in the first few weeks of life.

The invention further extends to the use of a probiotic bacterial strain and milk fat globule membrane in the manufacture of a nutritional composition for the prevention or treatment of pathogenic infections in a neonatal infant in the first few weeks of life.

In a further aspect, the invention extends to a method for promoting the maturation of the immune system of a neonatal infant in need thereof in the first few weeks of life.

The method comprises administering to the infant a therapeutic amount of a nutritional composition comprising a probiotic bacteria and milk fat globule membrane.

In a yet further aspect, the invention extends to a method for the prevention or treatment of pathogenic infections in a neonatal infant in need thereof in the first few weeks of life. It comprises administering to the infant a therapeutic amount of a nutritional composition comprising a probiotic bacteria and milk fat globule membrane.

In mammalian milk, the fat phase generally accounts for around 40 g/L and is mainly composed of triglycerides (96% of total fat), diglycerides (2% of total fat), and complex lipids (1% of total fat). Triglycerides synthesized in the smooth endoplasmic reticulum of the mammary alveolar cell coalesce into large droplets which migrate to the apical plasma membrane of the cell. The lipid droplets then push against and progressively become enveloped in the membrane of the mammary gland epithelial cells. These membranes, budded off around the milk lipids as they are being secreted by the cells, are named the milk fat globule membranes. The Milk fat globule membrane contains specific glycoproteins such as lactoferrin, mucins, lactadherin and xanthine oxidase as well as complex polar lipids such as glycerophospholipids and sphingolipids. Many of these components are present in human milk in much higher concentrations than in bovine milk.

The first interaction of probiotics with the host occurs at the level of the gut mucosa. Probiotics have been widely demonstrated to protect the host against infections and potentially improve specific disease outcomes. Among the key criteria often used for probiotic strain selection is their capacity to adhere to the intestinal mucosa. This appears to be important for blocking pathogen adherence in vitro and for modulating protective immune functions.

In studies examining the interaction of bovine milk fat globule membrane with intestinal epithelial cells (IEC) in vitro, the present inventors disrupted the milk fat globule membrane. Although bacteria were not directly detected in fractions of intact membranes, the disruption of the membranes by ultra-sound resulted in contamination of the IEC cultures. The bacteria appeared to come from the MFGM and not from the IEC cultures. In support of this, electron micrographs of bovine MFGM reveal the presence of bacterial cocci in chains (see FIG. 3). Without wishing to be bound by theory, the present inventors believe that bacteria binding to, or encapsulation of bacteria and/or their components within, the milk fat globule membrane may facilitate transport of the microbial components through the gastrointestinal system, ensure their delivery to appropriate sites in the mucosal tissues of the suckling neonate and, together with other factors in the milk fat globule membrane, modulate immunological processes. It is hypothesized that the association of MFGM and probiotics leads to potentiation (synergy) of the beneficial effects seen using probiotics or milk fat globule membrane alone.

The present invention reveals immune modulating properties of MFGM in association with probiotics that are beyond what could be achieved using the individual ingredients alone. Previous studies have shown that while probiotics and prebiotics are both recognised to have beneficial effects on health, their protective effects against diarrhoea in infants are lost when the two ingredients are combined (Chouraqui et al. 2007). Thus, the cooperation and/or synergy between the probiotic and MFGM observed in the present invention could not have been predicted.

The present invention reports that the combination of probiotics with MFGM on the one hand may limit some pro-inflammatory signals and as such, may limit tissue damage but on the other hand enhances mucosal protection by increasing production of secretory IgA by intestinal cells. This suggests that combining probiotics with MFGM leads to a physiological synergy by promoting distinct but complementary mechanisms which together provide an improved protection of the host. Furthermore, co-administration of probiotics and MFGM may impact biological responses in different tissue sites or in different cell types from those targeted by the individual components. For example, through their co-administration, the survival of live probiotics during intestinal transit as well as the homing of probiotics and/or their attachment to specific intestinal sites may be improved.

The present invention extends the use of MFGM and probiotics to further aspects of gut barrier maturation such as immune maturation. Furthermore, since the co-administration of probiotics and MFGM may also influence anti-inflammatory processes, the present invention extends to their combined use not only in infants but in at-risk populations irrespective of age. As such, it may not be necessary that a product containing such ingredients be the sole source of nutrition during the period of administration Mechanistically it can be hypothesized, for example, that MFGM is a significant source of lipids to the infant and that certain bacteria may increase the expression of molecules involved in lipid absorption. It follows that it should be possible to produce similar beneficial effects in formula-fed infants by supplementing the formula with probiotics and milk fat globule membrane. The probiotics can be pre-blended with MFGM before addition to the composition or the two preparations (probiotics, MFGM) can be added separately to the composition of the invention.

Preferably, the nutritional composition of the invention is an infant formula. The composition can be a children's food, liquid, semi-liquid or solid, especially for children between 0 and 7 years, or between 0 and 3 years. The composition can be a baby cereal. The composition of the invention can also be targeted to adolescent and adults suffering from particular physio-pathological conditions, especially those in need and/or having compromised gastro-intestinal systems and/or compromised immune/defense systems.

The probiotic is present in the formula in an amount equivalent to between $10^3$ and $10^{12}$ cfu/g of dry composition. The bacteria may be used live, inactivated or dead or even be present as fragments such as DNA or cell wall materials. In other words, the quantity of bacteria which the formula contains is expressed in terms of the equivalent colony forming units of bacteria irrespective of whether they are, all or partly, live, inactivated, dead or fragmented Preferably the probiotic is present in an amount equivalent to between $10^7$ to $10^{12}$ cfu/g of dry composition.

The probiotic bacterial strain may be any lactic acid bacteria or Bifidobacteria with established probiotic characteristics. The probiotic of the invention may be any probiotic bacterium or probiotic microorganism ("probiotics"), especially of human origin, in particular probiotics that have been or can be originated from, found in, extracted or isolated from milk upon excretion, preferably in human breast milk. Suitable probiotic lactic acid bacteria include *Lactobacillus rhamnosus* ATCC 53103 obtainable inter alia from Valio Oy of Finland under the trade mark LGG, *Lactobacillus rhamnosus* CGMCC 1.3724 (deposited in October 2004 at the China General Microbiological Culture Collection Center, Chinese Academy of Sciences, P.O. Box 2714, Beijing, China 100080), *Lactobacillus reuteri* ATCC 55730 and *Lactobacillus reuteri* DSM 17938 obtainable from Biogaia, *Lactobacillus fermentum* VRI 003 and *Lactobacillus paracasei* CNCM I-2116 (deposited on Jan. 12, 1999 at the Institut Pasteur, 28 rue du Docteur Roux, F-75024 Paris Cedex 15, France), *Lactobacillus johnsonii* CNCM I-1225 (deposited on Jun. 30, 1992 at the Institut Pasteur, 28 rue du Docteur Roux, F-75024 Paris Cedex 15, France), *Lactobacillus helveticus* CNCM I-4095 (deposited on Dec. 2, 2008 at the Institut Pasteur, 28 rue du Docteur Roux, F-75024 Paris Cedex 15, France), *Bifidobacterium breve* CNCM I-3865 (deposited on Nov. 15, 2007 at the Institut Pasteur, 28 rue du Docteur Roux, F-75024 Paris Cedex 15, France), and *Bifidobacterium longum* CNCM I-2618.

Suitable probiotic Bifidobacteria strains include *Bifidobacterium longum* ATCC BAA-999 (deposited on Jan. 29, 2001 at the Institut Pasteur, 28 rue du Docteur Roux, F-75024 Paris Cedex 15, France) sold by Morinaga Milk Industry Co. Ltd. of Japan under the trade mark BB536, the strain of *Bifidobacterium breve* sold by Danisco under the trade mark Bb-03, the strain of *Bifidobacterium breve* sold by Morinaga under the trade mark M-16V and the strain of *Bifidobacterium breve* sold by Institut Rosell (Lallemand) under the trade mark R0070. A particularly preferred *Bifidobacterium* strain is *Bifidobacterium lactis* CNCM I-3446 (deposited on Jun. 7, 2005 at the Institut Pasteur, 28 rue du Docteur Roux, F-75024 Paris Cedex 15, France) which may be obtained from the Christian Hansen Company of Denmark under the trade mark Bb12. A mixture of suitable probiotic lactic acid bacteria and Bifidobacteria may be used.

A variety of ingredients enriched in MFGM are commercially available. MFGM can be present in cream, buttermilk and whole milk. For product development use, buttermilk fractions are the source most often used due to their relatively high concentration of MFGM components. Examples of commercially available buttermilk products include buttermilk (product code 26048) from Land O'Lakes, Inc. Minn., buttermilk protein concentrate fractions from Fonterra Cooperative Group (Auckland, New Zealand); a phospholipid-rich fraction derived from MFGM from the Fonterra Cooperative Group Ltd. (Auckland, New Zealand); buttermilk from Büllinger Butterei (Büllingen, Belgium), Foster Farms Dairy (Modesto, Calif.), Dairy America Inc. (Fresno, Calif.), Dairy Farmers of America (Kansas City, Mo.); First Milk Ingredients Limited, Paisley, UK and Laban Up products of Gulf & Safa Dairies, United Arab Emirates. However, whey protein fractions enriched in MFGM are also commercially available. Examples include LACPRODAN® MFGM-10, a whey protein fraction enriched in MFGM produced by Arla Food Ingredients amba, Denmark. Other examples of material may include Promilk 602 E from Ingredia Lacto prosperité AG (Ingredia SA, Arras France), and from any suppliers containing MFGM (at least 1.5% of MFGM components; in order to be able to adjust the amount of MFGM to total protein).

Depending on the whey protein casein ratio (50/50, 70/30) in the infant formula, one source of MFGM casein based or milk based such as butter milk or Promilk 602E can be mixed in respect with this ratio with a whey protein.

The MFGM can comprise proteins, gangliosides and/or phospholipids or combination thereof.

The MFGM may originate from butter milk, butter milk fractions, defatted butter milk, delactosylated buttermilk, buttermilk fraction obtained by microfiltration, or ultrafiltration, fractions recovered from whey protein concentrate, sweet whey, acid whey, whey cream or fat associated fraction from whey containing phospholipids; and/or wherein said MFGM comprises sphingomyelin, phosphatidyl ethanolamine, phosphatidylcholine, phosphatidyl inositol, phosphatidyl serine, Cholesterol, gangliosides, Mucin1 (MUC 1), Xantine-oxidase/dehydrogenase, Periodicacid Schiff (PAS III), CD36, Butyrophilin(BTN), Adipophilin(ADPH), PAS 6/7, Fatty-acid binding protein(FABP), lactoferrin, lactaldherin, Butyrophilin, Adipophilin, peptide ETTVFENLPEK (SEQ ID: 1), peptide SFQLFGSPPGQR (SEQ ID: 2), peptide GSNFQLDQLQGR (SEQ ID: 3), peptide FQFIQVAGR597 (SEQ ID: 4), peptide IFIGNVNNSGLK (SEQ ID: 5), peptide INLFDTPLETQYVR (SEQ ID: 6), peptide TPLPLAGPPR (SEQ ID: 7), peptide EGQEQEGEEMAEYR (SEQ ID: 8), peptide SELLVDQYLPLTK (SEQ ID: 9) or combination thereof.

In one embodiment the composition of the invention comprises proteins able to bind to the probiotic.

The MFGM and the probiotic of the invention can interact together at the biological level. In particular, the MFGM can enhance or promote the biological effect of the probiotic. In one embodiment the MFGM enables the probiotic to have a biological effect that it would otherwise not have in the absence of MFGM. In one embodiment the MFGM and probiotics could have a synergistic effect in that the beneficial biological effect of the probiotic will be increased. Such a biological effect can comprise the effect on the maturation of the immune system and/or of the gut, the promotion of the anti-infection effect and/or the reduction of inflammation.

The probiotic can enhance or promote the biological effect of the MFGM. In one embodiment the probiotic enables the MFGM to have a biological effect that it would otherwise not have in the absence of the probiotic. In one embodiment the probiotic and the MFGM could have a synergistic effect in that the beneficial biological effect of the MFGM will be increased. Such a biological effect can comprise the effect on the maturation of the immune system and/or of the gut, the promotion of the anti-infection effect and/or the reduction of inflammation.

An infant formula according to the present invention may contain a protein source in an amount of not more than 3.7 or 2.0 g/100 kcal, preferably 1.8 to 2.0 g/100 kcal. The source and type of protein (for example from whey or from casein or mixture thereof) in the composition of the invention (i.e. the protein content not originating from MFGM) is not believed to be critical to the present invention provided that the minimum requirements for essential amino acid content are met and provided that satisfactory growth is ensured. However in one embodiment it is preferred that more than 50% or more than 60% by weight of the protein source is whey (hence insuring a best balanced amino-acid profile). Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in whatever proportions are desired.

Preferably, however, the major protein source is based on modified sweet whey. Sweet whey is a readily available by-product of cheese making and is frequently used in the manufacture of infant formulas based on cows' milk. However, sweet whey includes a component which is undesirably rich in threonine and poor in tryptophan called caseino-glycomacropeptide (CGMP). Removal of the CGMP from sweet whey results in a protein with a threonine content closer to that of human milk. This modified sweet whey can then be supplemented with those amino acids in respect of which it has a low content (principally histidine and tryptophan). A process for removing CGMP from sweet whey is described in EP 880902 and an infant formula based on this modified sweet whey is described in WO 01/11990. Using modified sweet whey as the principal protein in the protein source enables all essential amino acids to be provided at a protein content between 1.8 and 2.0 g/100 kcal. Such protein sources have been shown in animal and human studies to have a protein efficiency ratio, nitrogen digestibility, biological value and net protein utilization comparable to standard whey-adapted protein sources with a much higher protein content per 100 kcal and to result in satisfactory growth despite their reduced protein content. If modified sweet whey is used as the protein source, it is preferably supplemented by free histidine in an amount of from 0.1 to 1.5% by weight of the protein source.

The proteins may be intact or hydrolyzed or a mixture of intact and hydrolyzed proteins. It may be desirable to supply partially hydrolyzed proteins (degree of hydrolysis between 2 and 20%), for example for infants believed to be at risk of developing cows' milk allergy. If hydrolyzed proteins are required, the hydrolysis process may be carried out as desired and as is known in the art. For example, a whey protein hydrolysate may be prepared by enzymatically hydrolyzing the whey fraction in one or more steps. For an extensively hydrolyzed protein, the whey proteins may be subjected to triple hydrolysis using Alcalase 2.4 L (EC 940459), then Neutrase 0.5 L (obtainable from Novo Nordisk Ferment AG) and then pancreatin at 55° C. Alternatively, for a less hydrolyzed protein, the whey may be subjected to a two-stage hydrolysis using trypsin, chymotrypsin or pancreatin or mixtures thereof as described in EP 322589. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source. In one embodiment of the invention, the MFGM preparation is subjected to the same proteolytic treatment.

An infant formula according to the present invention may contain a carbohydrate source. Any carbohydrate source conventionally found in infant formulas such as lactose, saccharose, maltodextrin, starch and mixtures thereof may be used although the preferred source of carbohydrates is lactose. Preferably the carbohydrate sources contribute between 35 and 65% of the total energy of the formula.

An infant formula according to the present invention may contain a source of lipids, beside the lipids from the MFGM components. The lipid source may be any lipid or fat which is suitable for use in infant formulas. Preferred fat sources include high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. In total, the fat content is preferably such as to contribute between 30 to 55% of the total energy of the formula. The fat source preferably has a ratio of n-6 to n-3 fatty acids of about 5:1 to about 15:1; for example about 8:1 to about 10:1.

The infant formula may also contain all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin $B_1$, vitamin $B_2$, vitamin $B_6$, vitamin $B_{12}$, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

If necessary, the infant formula may contain emulsifiers and stabilizers such as soy lecithin, citric acid esters of mono- and di-glycerides, and the like. This is especially the case if the formula is provided in liquid form.

The infant formula may optionally contain other substances which may have a beneficial effect such as lactoferrin, nucleotides, nucleosides, and the like.

Preferably the infant formula also comprises a prebiotic. Suitable prebiotics include certain oligosaccharides, such as fructooligosaccharides (FOS) and galactooligosaccharides (GOS). A combination of prebiotics may be used such as 90% GOS with 10% short chain fructo-oligosaccharides such as the product sold under the trade mark Beneo® P95 or 10% inulin such as the product sold under the trade mark Beneo® HP, ST or HSI.

A particularly preferred prebiotic is a mixture of galacto-oligosaccharide(s), N-acetylated oligosaccharide(s) and sialylated oligosaccharide(s) in which the N-acetylated oligosaccharide(s) comprise 0.5 to 4.0% of the oligosaccharide mixture, the galacto-oligosaccharide(s) comprise 92.0 to 98.5% of the oligosaccharide mixture and the sialylated oligosaccharide(s) comprise 1.0 to 4.0% of the oligosaccharide mixture. This mixture is hereinafter referred to as "the preferred prebiotic mixture". Preferably, a composition for use according to the invention contains from 2.5 to 15.0 wt % of the preferred prebiotic mixture on a dry matter basis with the proviso that the composition comprises at least 0.02 wt % of an N-acetylated oligosaccharide, at least 2.0 wt % of a galacto-oligosaccharide and at least 0.04 wt % of a sialylated oligosaccharide.

Suitable N-acetylated oligosaccharides include GalNAcα1,3Galβ1,4Glc and Galβ1,6GalNAcα1,3Galβ1,4Glc. The N-acetylated oligosaccharides may be prepared by the action of glucosaminidase and/or galactosaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced by fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerisation (DP) from DP=1 onwards. Another option is the chemical conversion of keto-hexoses (e.g. fructose) either free or bound to an oligosaccharide (e.g. lactulose) into N-acetylhexosamine or an N-acetylhexosamine containing oligosaccharide as described in Wrodnigg, T. M.; Stutz, A. E. (1999) Angew. Chem. Int. Ed. 38:827-828.

Suitable galacto-oligosaccharides include Galβ1,6Gal, Galβ1,6Galβ1,4Glc Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc, Galβ1,3Galβ1,3Galβ1,4Glc, Galβ1,4Galβ1,4Glc and Galβ1,4Galβ1,4Galβ1,4Glc. Synthesised galacto-oligosaccharides such as Galβ1,6Galβ1,4Glc Galβ1,6Galβ1,6Glc, Galβ1,3Galβ1,4Glc, Galβ1,6Galβ1,6Galβ1,4Glc, Galβ1,6Galβ1,3Galβ1,4Glc and Galβ1,3Galβ1,6Galβ1,4Glc, Galβ1, 4Galβ1,4Glc and Galβ1,4Galβ1,4Galβ1,4Glc and mixtures thereof are commercially available under the trade marks Vivinal® and Elix'or®. Other suppliers of oligosaccharides are Dextra Laboratories, Sigma-Aldrich Chemie GmbH and Kyowa Hakko Kogyo Co., Ltd. Alternatively, specific glycoslytransferases, such as galactosyltransferases may be used to produce neutral oligosaccharides.

Suitable sialylated oligosaccharides include NeuAcα2,3Galβ1,4Glc and NeuAcα2,6Galβ1,4Glc. These sialylated oligosaccharides may be isolated by chromatographic or filtration technology from a natural source such as animal milks. Alternatively, they may also be produced by biotechnology using specific sialyltransferases either by enzyme based fermentation technology (recombinant or natural enzymes) or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerization (DP) from DP=1 onwards.

The infant formula may be prepared in any suitable manner. For example, an infant formula may be prepared by blending together the protein source, the carbohydrate source, and the fat source in appropriate proportions. If used, the emulsifiers may be included in the blend. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce undesired viable bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger.

The liquid mixture may then be cooled to about 60° C. to about 85° C.; for example by flash cooling. The liquid mixture may then be homogenized; for example in two stages at about 7 MPa to about 40 MPa in the first stage and about 2 MPa to about 14 MPa in the second stage. The homogenized mixture may then be further cooled to add any heat sensitive components; such as vitamins and minerals. The pH and solids content of the homogenized mixture is conveniently standardized at this point.

The homogenized mixture is transferred to a suitable drying apparatus such as a spray drier or freeze drier and converted to powder. The powder should have a moisture content of less than about 5% by weight.

The selected probiotic(s) may be cultured according to any suitable method and prepared for addition to the infant formula by freeze-drying or spray-drying for example. Alternatively, bacterial preparations can be bought from specialist suppliers such as Christian Hansen and Morinaga already prepared in a suitable form for addition to food products such as infant formula.

The selected probiotic may be blended to any MFGM preparation before drying. This blend could be homogenized to favor association between MFGM, probiotics and probiotic(s). After drying the blend can be used as a module (added to liquid formula) or MFGM can be mixed to formula powder.

Probiotic powder and MFGM powders could be mixed by dry mixing, forming a specific blend. This blend could be added together in the final infant formula powder. Alternately the blend can be added extemporary to the liquid formula.

MFGM preparation could also be added during formula process before homogenization and pasteurization/heat treatment sterilization up to UHT treatment for a liquid formula. After drying the probiotic could be incorporated by dry mixing MFGM preparation could also be considered as a good natural emulsifier to reduce the emulsifiers conventionally used in Infant Formula or nutritional compositions. In one embodiment the probiotic and/or the MFGM preparations care added separately or together to a ready-to-drink or ready-to-dilute nutritional composition such as a powder infant formula. Such addition(s) can occur during one of the last process steps of the manufacturing/packaging of the composition or can occur just before the use of the composition by the intended user. In such instance the MFGM preparation and/or the probiotic preparation can be provided separately from the powder or liquid nutritional composition.

EXAMPLE 1

An example of the composition of an infant formula according to the present invention is given below (table 1). This composition is given by way of illustration only.

TABLE 1

Infant formula according to the invention

| Nutrient | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| *Bifidobacterium lactis* CNCM I-3446 | 2.10$^7$ cfu/g of powder, live bacteria | |
| MFGM: Lacprodan MFGM 10 from Arla Food Ingredients (Arla Foods Ingredients amba, Skanderborgvej 277, 8260 Viby J (Denmark). | 4% (w/w) | |

Alternatively, in another example, the MFGM ingredient can be used in such amount to achieve a ratio MFGM/total protein of 0.5%.

EXAMPLE 2

The following example presents scientific data developing and supporting the concept of interactions between probiotics and MFGM in mammals breast milk. It follows that compositions comprising both MFGM and probiotics present an advantageous effect.

In is known from prior art that a low dose of micro-organisms and a range of microbial DNA are contained in human breast milk and are associated with the milk cellular compartment. The inventors have herewith hypothesized that bacteria in milk may be associated with other milk compartments besides the cellular component. For example, they may be transported within the MFGM or casein micelles. The inventors have analyzed the presence of microbial DNA signals in various fractions of mammals' milk. In FIGS. 1 and 2, temporal Temperature Gradient-gel Electrophoresis (TTGE) has been used. The experiments detected that strong bacterial DNA signals were also found in the cream fraction of the milk (FIGS. 1 and 2). The finding supports the concept that the MFGM contains bacterial components and/or that the MFGM may bind to or 'envelop' the bacteria in the milk.

Further the inventors have investigated the transportation of microbial load. FIG. 3 shows microbial components co-located with MFGM. The inventors hypothesize that bacterial binding to or encapsulation of bacteria and/or their components within the MFGM, may facilitate transport of the microbial components through the gastrointestinal system. The inventors believe that this may enhance their delivery to appropriate sites in the mucosal tissues of the suckling neonate. Together with other factors in the MFGM it may further modulate immunological processes.

EXAMPLE 3

Proteomics studies of the human MFGM both internally and externally, have identified several proteins which are considered to influence bacterial growth or survival, are involved in the recognition of and/or response to microbes or their components, or are known to interact with other proteins which do so. For example, Toll-like receptors (TLRs) are a class of cell membrane receptors that recognise structurally conserved molecules derived from microbes and activate immune responses. They are believed to play a key role in the innate immune system. The MFGM comprises molecules which are co-receptors/molecules of TLR signalling complexes as well as potential ligands for these complexes.

Differential responses to pro-inflammatory factors have been observed in vitro, suggesting that the MFGM and/or MFGM fractions may support immune defense mechanisms without promoting exaggerated responses (see table 2).

TABLE 2

Effect of various fractions containing MFGM (whole or digest) on the expression of factors, showing up-regulation or down-regulation.

| Fraction | Peripheral blood mononuclear cells | | Intestinal epithelial cells |
|---|---|---|---|
| | IFN-induced IL-12p70 | LPS-induced TNF-α | NF-κB activation TNF-induced |
| MFGM | ↓ | ↑ | ↑ |
| MFGM Digest | — | ↑ | ↑ |

Taken together, it is plausible that delivery of bacteria and/or bacterial components in the presence of MFGM may influence the composition of the intestinal microbiota. It could further modulate immune responses in the recipient host such that there is tolerance to components of the normal microbiota and dietary antigens and protection against potential pathogens or danger signals.

Combinations of MFGM and/or MFGM fractions with probiotic organisms and/or microbial components could be used to educate the immune system and provide protection against early life infections.

Overall, MFGM and/or MFGM fractions, when associated with probiotics and/or probiotic components, could promote the interaction of probiotics with the host and modulate downstream processes involved in defense mechanisms. The inventors believe that MFGM and/or MFGM fractions, in combination with probiotics and/or probiotic components, may help modulate the neonatal microbiota composition, support immune development and trigger efficient protective host defense reactions. This can include immune responses, against various pathogens or other environmental danger. This can be linked to capacity of the probiotics to confer optimal delivery to the host and/or promote host responsiveness to exogenous and endogenous signals.

EXAMPLE/EXPERIMENTAL DATA 4

The Interactions of MFGM fractions with the host and potential synergistic effect with probiotics was evaluated in vitro in a system mimicking the gut mucosa (FIG. 4). The data support a beneficial effect of a combination of MFGM and probiotics on host defenses against infections and modulation of inflammatory conditions.

HT29Cl34 NFkB Reporter Assays:

The HT-29 (human colonic epithelial cells) cell line expresses endogenous TLRs. TLR signalling activates the NF-kB transcription factor either through MyD88 or TRIF adaptator proteins and leads to expression of inflammatory genes. HT-29 cell lines were also transfected with a reporter construct, such that the secreted alkaline phosphatase (SeAP) is expressed under the control of a NF-kB inducible promoter. This transfected cell line, HT-29Cl134, has been developed at the Nestlé Research Center. TLR stimulation of these cells leads to NF-kB activation and subsequent secretion of alkaline phosphatase into the culture supernatantin To assess TLR-mediated inflammation, the HT-29Cl134 reporter gene system was used to measure levels of NF-kB activation after a pre-treatment with *Bifidobacterium lactis* NCC2818 (*B. lactis*) at $10e^6$ or $10e^7$ CFU/mL and/or MFGM preparation at 50 ug/mL or 100 ug/mL final, followed by incubation with or without LPS (100 ng/mL). SeAP activity was assessed by a fluorometric assay and expressed in relative fluorescent units. *Bifidobacterium lactis* NCC2818 (*B. lactis*) was selected as a representative of the bifidobacterial species that are important early colonizers of the infant gut. FIG. 5 shows the cumulative, synergistic effect obtained by combining MFGM and probiotics in this model MFGM alone decreases the responsiveness of epithelial cells to an endotoxin challenge. MFGM+probiotics (*B. lactis*) exhibits a stronger effect than MFGM alone or probiotics alone (FIG. 5 upper and lower panels).

B and T Cell Stimulation Assays:

Lymphocyte suspensions were prepared from pooled mesenteric and inguinal lymph nodes isolated from 6-8 week old C57BL/6 mice. Cells were suspended in IMDM culture medium supplemented with $5\times10^{-5}$ M β-mercaptoethanol, 1 mM glutamine, 100 U/mL penicillin, 100 µg/mL streptomycin and 10% FCS. For anti-CD3 (T-cell specific) and anti-CD40 (B-cell specific) stimulation, 96-well flat-bottom plates were coated with 50 µL PBS containing 2.5 ug/mL anti-CD3 (clone: 2C11) or 5 ug/mL anti-CD40 (clone: FGK-45) 1-3 h at 37° C. After extensive washing, serial 3-fold dilutions of lymph node cell suspensions were added per well. After 3 days, 1 μCi/well ³H-thymidine was added for the last 18 h prior to harvesting. When said NCC2818 (*B. lactis*) obtained from standard cultures were added to the well together with the MFGM preparation at MOI 100 and/or 100 ug/mL final concentration. Results of the assay performed with optimal titration of lymphoid cells (111'000 cells/well) are presented in FIGS. 6 and 7. The results highlight the synergistic effect of a probiotic with MFGM.

EXAMPLE 5

The interactions of MFGM fractions with the host and potential synergistic and long lasting effects in association with probiotics were evaluated in vivo in a mouse model of neonatal maturation. The data support a beneficial effect of a combination of MFGM and probiotics on non-specific adaptive host defenses against infections via an increase in secretory mucosal IgA.

Recently weaned mice (28 day old) were fed for 1 week (A) and 4 weeks (B) as below:
- Group 1: Placebo (maltodextrin)
- Group 2: *Bifidobacterium lactis* BL818 (108 CFU/day)
- Group 3: *Bifidobacterium lactis* BL818 (108 CFU/day)+ MFGM
- Group 4: MFGM MFGM was administered daily at a dose of 0.6 mg/g of body weight. The ingredients, *B. lactis* and/or MFGM, were administrated orally. Recently weaned animals were used to avoid an effect of the MFGM naturally present in mouse breastmilk.

IgA-secreting cell numbers in Peyer's patches cell suspensions were evaluated in 10 animals per group using a standard ELISPOT protocol. Our data (FIG. 8) show that MFGM can have strong effects on adaptive immune B cells. Indeed, we observed a significant increase in the number of intestinal IgA-secreting cells isolated from the Peyer's patches of mice fed with MFGM and/or probiotics. Interestingly, we observed that the combination of MFGM and *B. lactis* significantly increases the IgA-secreting mucosal B cells numbers after 28 days of feeding and the numbers are greater than those observed after feeding of the individual ingredients. Even more interestingly, we observed a long-lasting immune boost effect of MFGM and *B. lactis* feeding. More specifically, the increase in IgA-secreting mucosal B cell numbers persists and indeed, is further increased 84 days after feeding of the ingredients was stopped (day 112). Importantly, the effect of the combination of probiotics and MFGM was significantly higher than that obtained with the individual ingredients, which demonstrates a synergistic effect when feeding the combination of probiotics and MFGM.

The invention claimed is:

1. A nutritional composition comprising a probiotic in an amount of $10^3$ to $10^{12}$ cfu/g of the composition and milk fat globule membrane (MFGM) in an amount between 0.01 g and 7 g of MFGM per 100 g of composition (w/w) wherein the MFGM enhances the biological effect of the probiotic, and the probiotic is *Bifidobacterium lactis* CNCM I-3446.

2. The nutritional composition of claim 1 wherein the composition is selected from the group consisting of an infant formula, infant cereal, and baby food.

3. The nutritional composition of claim 1 wherein the MFGM comprises proteins or bioactive proteins able to bind with or biologically interact with the probiotic.

4. The nutritional composition of claim 1 comprising proteins, wherein the MFGM is present in an amount of between 0.1% and 10% w/w of the proteins.

5. The nutritional composition of claim 1 wherein the MFGM comprises gangliosides and/or phospholipids able to bind with or biologically interact with the probiotic.

6. The nutritional composition of claim 1 wherein the composition comprises a prebiotic.

7. The composition of claim 1 wherein the MFGM has been treated by food grade proteolytic enzyme.

8. The nutritional composition of claim 1, wherein the MFGM comprises an ingredient selected from the group consisting of sphingomyelin, phosphatidyl ethanolamine, phosphatidylcholine, phosphatidyl inositol, phosphatidyl serine, Cholesterol, gangliosides, Mucin1 (MUC 1), Xantine-oxidase/dehydrogenase, Periodicacid Schiff (PAS III), CD36, Butyrophilin(BTN), Adipophilin(ADPH), PAS 6/7, Fatty-acid binding protein(FABP), lactoferrin, lactaldherin, Butyrophilin, Adipophilin, peptide ETTVFENLPEK (SEQ ID: 1), peptide SFQLFGSPPGQR (SEQ ID: 2), peptide GSNFQLDQLQGR (SEQ ID: 3), peptide FQFIQVAGR597 (SEQ ID: 4), peptide IFIGNVNNSGLK (SEQ ID: 5), peptide INLFDTPLETQYVR (SEQ ID: 6), peptide TPLPLAGPPR (SEQ ID: 7), peptide EGQEQEGEEMAEYR (SEQ ID: 8), peptide SELLVDQYLPLTK (SEQ ID: 9) and combinations thereof.

9. The nutritional composition of claim 1 wherein the composition is an infant formula.

10. The nutritional composition of claim 9 wherein the infant formula comprises a protein source selected from the group consisting of whey, casein and a combination thereof, further comprises a lipid source additional to the MFGM, and further comprises a carbohydrate source.

11. The nutritional composition of claim 10 wherein the protein source is 1.8 to 2.0 g/100 kcal of the infant formula.

12. The nutritional composition of claim 1 wherein the MFGM is in powder form.

* * * * *

SEQUENCE LISTING

```
<160> NUMBER OF SEQ ID NOS: 9

<210> SEQ ID NO 1
<211> LENGTH: 11
<212> TYPE: PRT
<213> ORGANISM: Artificial sequence
<220> FEATURE:
<223> OTHER INFORMATION: Synthesized: peptide 1

<400> SEQUENCE: 1

Glu Thr Thr Val Phe Glu Asn Leu Pro Glu Lys
1               5                   10

<210> SEQ ID NO 2
<211> LENGTH: 12
<212> TYPE: PRT
<213> ORGANISM: Artificial sequence
<220> FEATURE:
<223> OTHER INFORMATION: Synthesized: peptide 2

<400> SEQUENCE: 2

Ser Phe Gln Leu Phe Gly Ser Pro Pro Gly Gln Arg
1               5                   10

<210> SEQ ID NO 3
<211> LENGTH: 12
<212> TYPE: PRT
<213> ORGANISM: Artificial sequence
<220> FEATURE:
<223> OTHER INFORMATION: Synthesized: peptide 3

<400> SEQUENCE: 3

Gly Ser Asn Phe Gln Leu Asp Gln Leu Gln Gly Arg
1               5                   10

<210> SEQ ID NO 4
<211> LENGTH: 9
<212> TYPE: PRT
<213> ORGANISM: Artificial sequence
```

```
<220> FEATURE:
<223> OTHER INFORMATION: Synthesized: peptide 4

<400> SEQUENCE: 4

Phe Gln Phe Ile Gln Val Ala Gly Arg
1               5

<210> SEQ ID NO 5
<211> LENGTH: 12
<212> TYPE: PRT
<213> ORGANISM: Artificial sequence
<220> FEATURE:
<223> OTHER INFORMATION: Synthesized: peptide 5

<400> SEQUENCE: 5

Ile Phe Ile Gly Asn Val Asn Asn Ser Gly Leu Lys
1               5                   10

<210> SEQ ID NO 6
<211> LENGTH: 14
<212> TYPE: PRT
<213> ORGANISM: Artificial sequence
<220> FEATURE:
<223> OTHER INFORMATION: Synthesized: peptide 6

<400> SEQUENCE: 6

Ile Asn Leu Phe Asp Thr Pro Leu Glu Thr Gln Tyr Val Arg
1               5                   10

<210> SEQ ID NO 7
<211> LENGTH: 10
<212> TYPE: PRT
<213> ORGANISM: Artificial sequence
<220> FEATURE:
<223> OTHER INFORMATION: Synthesized: peptide 7

<400> SEQUENCE: 7

Thr Pro Leu Pro Leu Ala Gly Pro Pro Arg
1               5                   10

<210> SEQ ID NO 8
<211> LENGTH: 14
<212> TYPE: PRT
<213> ORGANISM: Artificial sequence
<220> FEATURE:
<223> OTHER INFORMATION: Synthesized: peptide 8

<400> SEQUENCE: 8

Glu Gly Gln Glu Gln Glu Gly Glu Glu Met Ala Glu Tyr Arg
1               5                   10

<210> SEQ ID NO 9
<211> LENGTH: 13
<212> TYPE: PRT
<213> ORGANISM: Artificial sequence
<220> FEATURE:
<223> OTHER INFORMATION: Synthesized: peptide 9

<400> SEQUENCE: 9

Ser Glu Leu Leu Val Asp Gln Tyr Leu Pro Leu Thr Lys
1               5                   10
```